(12) United States Patent
Jeon et al.

(10) Patent No.: US 11,529,124 B2
(45) Date of Patent: Dec. 20, 2022

(54) ARTIFACT REMOVING METHOD AND DIAGNOSTIC APPARATUS USING THE SAME

(71) Applicant: SAMSUNG ELECTRONICS CO., LTD., Suwon-si (KR)

(72) Inventors: Kang-won Jeon, Yongin-si (KR); Hyun-taek Lee, Seoul (KR); Mun-kyeong Hwang, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 1765 days.

(21) Appl. No.: 14/990,971

(22) Filed: Jan. 8, 2016

(65) Prior Publication Data

US 2016/0287216 A1 Oct. 6, 2016

Related U.S. Application Data

(60) Provisional application No. 62/140,771, filed on Mar. 31, 2015.

(30) Foreign Application Priority Data

Jun. 11, 2015 (KR) ........................ 10-2015-0082573

(51) Int. Cl.
*A61B 8/08* (2006.01)
*G01S 7/52* (2006.01)
(Continued)

(52) U.S. Cl.
CPC .......... *A61B 8/5269* (2013.01); *A61B 8/5207* (2013.01); *G01S 7/52077* (2013.01);
(Continued)

(58) Field of Classification Search
CPC ......... A61B 8/5269; A61B 8/461; A61B 8/14; G01S 7/52095
See application file for complete search history.

(56) References Cited

U.S. PATENT DOCUMENTS 5,148,810 A * 9/1992 Maslak ................ G01N 29/262
600/437
5,976,089 A * 11/1999 Clark .................. G01S 7/52017
600/447

(Continued)

FOREIGN PATENT DOCUMENTS

JP 2002-537048 A 11/2002
JP 2005-323894 A 11/2005
(Continued)

OTHER PUBLICATIONS

Communication dated May 26, 2022 issued by the Korean Intellectual Property Office in counterpart English Korean Application No. 10-2015-0082573.

*Primary Examiner* — Sanjay Cattungal
(74) *Attorney, Agent, or Firm* — Sughrue Mion, PLLC

(57) ABSTRACT

An ultrasound imaging apparatus includes an ultrasound transceiver configured to transmit an ultrasound signal to an object and receive an ultrasound echo signal reflected from the object, based on a beamforming parameter of the ultrasound imaging apparatus; and an image processor configured to generate scanning lines forming a frame based on the received ultrasound echo signal, generate sub-frames by sorting the scanning lines into respective groups having the scanning lines with similar properties, based on the beamforming parameter, perform image-processing of the generated sub-frames, and recombine the scanning lines from the image-processed sub-frames to generate an ultrasound medical image corresponding to the frame.

10 Claims, 10 Drawing Sheets

(51) Int. Cl.
*A61B 8/14* (2006.01)
*A61B 8/00* (2006.01)

(52) U.S. Cl.
CPC ...... *G01S 7/52088* (2013.01); *G01S 7/52095* (2013.01); *A61B 8/14* (2013.01); *A61B 8/461* (2013.01); *A61B 8/54* (2013.01)

(56) References Cited

U.S. PATENT DOCUMENTS

| | | | | |
|---|---|---|---|---|
| 6,139,498 | A * | 10/2000 | Katsman | G01S 7/52034 600/443 |
| 6,228,031 | B1 | 5/2001 | Hwang et al. | |
| 6,282,963 | B1 | 9/2001 | Haider | |
| 6,602,194 | B2 | 8/2003 | Roundhill et al. | |
| 6,749,569 | B1 * | 6/2004 | Pellegretti | A61B 8/08 600/441 |
| 7,399,279 | B2 | 7/2008 | Abend et al. | |
| 7,881,774 | B2 | 2/2011 | Kobayashi | |
| 8,475,380 | B2 | 7/2013 | Kristoffersen et al. | |
| 2004/0054284 | A1 * | 3/2004 | Cai | G01S 7/52034 600/443 |
| 2005/0096544 | A1 * | 5/2005 | Hao | G01S 15/8959 600/447 |
| 2005/0131302 | A1 * | 6/2005 | Poland | A61B 8/14 600/459 |
| 2005/0283079 | A1 * | 12/2005 | Steen | A61B 8/4483 600/447 |
| 2007/0038083 | A1 * | 2/2007 | Srinivasan | G01S 15/584 600/437 |
| 2007/0049825 | A1 * | 3/2007 | Lee | G01S 15/8995 600/437 |
| 2007/0078347 | A1 * | 4/2007 | Srinivasan | G01S 15/8979 600/465 |
| 2008/0208061 | A1 * | 8/2008 | Halmann | G01S 7/52085 600/459 |
| 2009/0069675 | A1 * | 3/2009 | Srinivasan | G01S 15/8979 600/437 |
| 2009/0306503 | A1 * | 12/2009 | Srinivasan | A61B 8/00 600/441 |
| 2009/0306512 | A1 * | 12/2009 | Loftman | G01S 7/52046 600/447 |
| 2011/0005322 | A1 * | 1/2011 | Ustuner | G01N 29/069 73/627 |
| 2011/0208056 | A1 * | 8/2011 | Datta | A61B 8/5223 600/441 |
| 2012/0053461 | A1 * | 3/2012 | Li | G01S 7/52074 600/441 |
| 2012/0089027 | A1 * | 4/2012 | Andreuccetti | G01S 15/8984 600/443 |
| 2012/0152021 | A1 * | 6/2012 | Ma | A61B 8/06 73/632 |
| 2012/0250454 | A1 * | 10/2012 | Rohling | G01N 29/2406 367/7 |
| 2014/0180111 | A1 * | 6/2014 | Gopinathan | A61B 8/4483 600/447 |
| 2015/0245818 | A1 * | 9/2015 | Zhai | A61B 8/5269 600/453 |
| 2016/0287216 | A1 | 10/2016 | Jeon et al. | |
| 2017/0285156 | A1 * | 10/2017 | Yigang | G01S 15/8927 |

FOREIGN PATENT DOCUMENTS

| | | |
|---|---|---|
| JP | 2007-20908 A | 2/2007 |
| KR | 10-2001-0077539 A | 8/2001 |

* cited by examiner

ARTIFACT REMOVING METHOD AND DIAGNOSTIC APPARATUS USING THE SAME

CROSS-REFERENCE TO RELATED APPLICATIONS

This application claims the benefit of U.S. Provisional Application No. 62/140,771, filed Mar. 31, 2015, and claims priority from Korean Patent Application No. 10-2015-0082573, filed on Jun. 11, 2015, in the Korean Intellectual Property Office. The disclosures of the above-identified applications are incorporated herein in their entireties by reference.

BACKGROUND

1. Field

One or more exemplary embodiments relate to removing an artifact from a medical image.

2. Description of the Related Art

Ultrasound diagnostic apparatuses transmit ultrasound signals generated by transducers included in a probe to an object and receive echo signals reflected from the object, thereby obtaining an image of the object (e.g., soft tissues or blood flow). In particular, ultrasound diagnostic apparatuses are used for medical purposes including observation of the interior of an object, detection of foreign substances, and diagnosis of damage to the object. Such ultrasound diagnostic apparatuses have high stability, display images in real time, and are safe due to the lack of radioactive exposure, compared to X-ray apparatuses. Therefore, ultrasound diagnostic apparatuses are widely used.

A related art ultrasound diagnostic apparatus generates one scanning line from a one-time transmitted ultrasound signal and thus respective scanning lines have the same scanning line properties.

Also, a related art ultrasound diagnostic apparatus may generate a plurality of scanning lines from a one-time transmitted and/or received ultrasound signal and thus adjacent scanning lines have different scanning line properties. Since the scanning line properties are different among adjacent scanning lines in a frame, an artifact, such as a strict artifact, may be generated when the frame is image-processed.

SUMMARY

Exemplary embodiments may address at least the above problems and/or disadvantages and other disadvantages not described above. Also, the exemplary embodiments are not required to overcome the disadvantages described above, and an exemplary embodiment may not overcome any of the problems described above.

One or more exemplary embodiments provide a method of preventing generation of an artifact in an ultrasound image based on a beamforming parameter, and a diagnostic apparatus using the method.

In accordance with an aspect of an exemplary embodiment, a medical imaging apparatus includes an ultrasound transceiver transmitting an ultrasound signal to an object and receiving an ultrasound echo signal reflected from the object, based on a beamforming parameter set in an ultrasound imaging apparatus, and an image processor generating a plurality of scanning lines forming a frame based on a received ultrasound echo signal, generating at least one sub-frame by classifying the plurality of scanning lines into at least one group, based on the beamforming parameter, performing image-processing with respect to a generated sub-frame, and recombining scanning lines in an image-processed sub-frame to generate an ultrasound image corresponding to the frame.

The medical imaging apparatus may further include a display that displays a generated ultrasound image.

The beamforming parameter may include at least one of a beamforming method, beam steering direction, a depth of a focal point, a frequency of an ultrasound signal, and a size of an aperture of the medical imaging apparatus.

The ultrasound signal may include a first ultrasound signal and a second ultrasound signal respectively having focal points at different positions, and the image processor may generate the plurality of scanning lines by generating a first scanning line based on a first ultrasound echo signal corresponding to the first ultrasound signal, generating a second scanning line based on a second ultrasound echo signal corresponding to the second ultrasound signal, and generating at least one additional third scanning line by interpolating the first scanning line and the second scanning line.

The image processor may generate a plurality of scanning lines corresponding to the ultrasound signal, based on the received ultrasound echo signal.

The image processor may generate at least one sub-frame by obtaining a type of a beamforming method used to generate the plurality of scanning lines, based on the beam beamforming parameter, and classifying the plurality of scanning lines into at least one group to generate scanning lines having similar scanning line properties in one group, based on a type of the obtained beamforming method.

The image processor may generate the ultrasound image by rearranging scanning lines in the image-processed sub-frame in an order of the plurality of scanning lines before being classified into the group.

In accordance with an aspect of an exemplary embodiment, a method of displaying a medical image includes transmitting an ultrasound signal to an object and receiving an ultrasound echo signal reflected from the object, based on a beamforming parameter set in an medical imaging apparatus, generating a plurality of scanning lines forming a frame based on a received ultrasound echo signal, generating at least one sub-frame by classifying the plurality of scanning lines into at least one group, based on the beamforming parameter, performing image-processing with respect to a generated sub-frame, and recombining scanning lines in an image-processed sub-frame to generate an ultrasound image corresponding to the frame.

The method may further include displaying a generated ultrasound image.

The beamforming parameter may include at least one of a beamforming method, beam steering direction, a depth of a focal point, a frequency of an ultrasound signal, and a size of an aperture of the medical imaging apparatus.

The ultrasound signal may include a first ultrasound signal and a second ultrasound signal respectively having focal points at different positions, and the generating of a plurality of scanning lines forming a frame based on a received ultrasound echo signal may include generating a first scanning line based on a first ultrasound echo signal corresponding to the first ultrasound signal, generating a second scanning line based on a second ultrasound echo signal corresponding to the second ultrasound signal, and generating at least one additional third scanning line by interpolating the first scanning line and the second scanning line, to generate the plurality of scanning lines.

In the generating of a plurality of scanning lines forming a frame based on a received ultrasound echo signal, a plurality of scanning lines corresponding to the ultrasound signal may be generated based on the received ultrasound echo signal.

In the generating of at least one sub-frame by classifying the plurality of scanning lines into at least one group, based on the beamforming parameter, at least one sub-frame may be generated by obtaining a type of a beamforming method used to generate the plurality of scanning lines, based on the beam beamforming parameter, and classifying the plurality of scanning lines into at least one group to generate scanning lines having similar scanning line properties in one group, based on a type of the obtained beamforming method.

In the recombining of scanning lines in an image-processed sub-frame to generate an ultrasound image corresponding to the frame, the ultrasound image may be generated by rearranging scanning lines in the image-processed sub-frame in an order of the plurality of scanning lines before being classified into the group.

BRIEF DESCRIPTION OF THE DRAWINGS

The above and/or other aspects will become apparent by describing certain exemplary embodiments, with reference to the accompanying drawings, in which.

DETAILED DESCRIPTION

Figure 1:
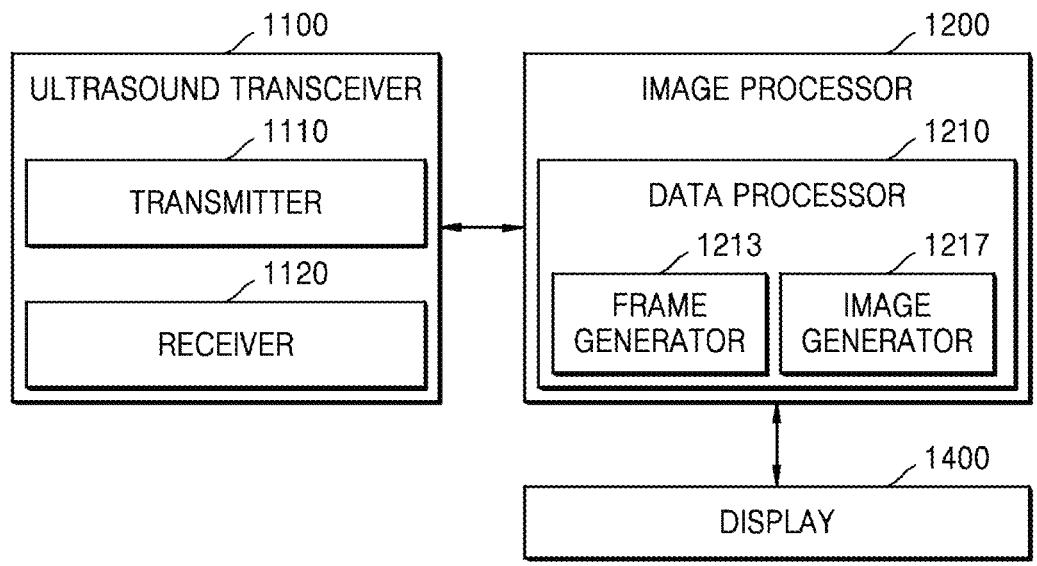
FIG. 1 is a block diagram of an ultrasound diagnostic apparatus according to an exemplary embodiment.

Certain exemplary embodiments are described in greater detail below with reference to the accompanying drawings.

In the following description, the same drawing reference numerals are used for the same elements even in different drawings. The matters defined in the description, such as detailed construction and elements, are provided to assist in a comprehensive understanding of exemplary embodiments. Thus, it is apparent that exemplary embodiments can be carried out without those specifically defined matters. Also, well-known functions or constructions are not described in detail since they would obscure exemplary embodiments with unnecessary detail.

As used herein, the term "and/or" includes any and all combinations of one or more of the associated listed items. Expressions such as "at least one of," when preceding a list of elements, modify the entire list of elements and do not modify the individual elements of the list.

The terms used herein have been selected from currently widely used general terms in consideration of the functions of exemplary embodiments. However, the terms may vary according to the intention of one of ordinary skill in the art, case precedents, and the advent of new technologies. Also, for special cases, meanings of the terms selected by the applicant are described in detail in the description section. Accordingly, the terms used herein are defined based on their meanings in relation to the contents discussed throughout the specification, not by their simple meanings.

Throughout the specification, it will also be understood that when a component "includes" an element, unless there is another opposite description thereto, it should be understood that the component does not exclude another element and may further include another element. In addition, terms such as ". . . unit", ". . . module", or the like refer to units that perform at least one function or operation, and the units may be implemented as hardware or software or as a combination of hardware and software.

Throughout the specification, an "ultrasound image" refers to an image of an object, which is obtained using ultrasound waves. Furthermore, an "object" may be a human, an animal, or a part of a human or animal. For example, an object may include organs such as the liver, the heart, the womb, the brain, a breast, the abdomen, etc., or blood vessels. Also, the object may be a phantom. The phantom means a material having a density, an effective atomic number, and a volume that are approximately the same as those of an organism. For example, the phantom may be a spherical phantom having properties similar to a human body.

Throughout the specification, a "user" may be, but is not limited to, a medical expert, for example, a medical doctor, a nurse, a medical laboratory technologist, or a medical imaging expert, or a technician who repairs medical apparatuses.

Also, throughout the specification, a beam pattern signifies characteristics of an ultrasound beamforming a scanning line affecting in a space at a particular position and generally has a shape similar to a sinc function. When transceiving conditions of an ultrasound signal are the same, an ultrasound diagnostic apparatus performs the same forming operation. Accordingly, beam patterns may be the same when beamforming parameters are the same and may be different from each other when the beamforming parameters are different from each other. A beamforming parameter may include at least one of a beamforming method, a beam steering direction, a depth of a focal point, a frequency of an ultrasound signal, and a size of an aperture, but not limited thereto.

Also, throughout the specification, scanning line properties may signify a method of generating a scanning line or may be referred to as a beam pattern.

For example, scanning line properties may differ according to whether a scanning line is generated directly from an ultrasound echo signal or by interpolating previously generated scanning lines. Also, even when a scanning line is generated directly from an ultrasound echo signal, the scanning line properties may differ according to whether one scanning line or a plurality of scanning lines are generated based on one transmitting beam. Also, when a plurality of scanning lines are generated based on one transmitting beam, scanning line properties of the generated scanning lines may be different from each other.

Also, even when one scanning line is generated based on one transmitting beam, scanning line properties of scanning lines may be different from each other when transmitting beams have different beamforming parameters.

Also, throughout the specification, a frame may signify a plurality of scanning lines forming one ultrasound image.

FIG. 1 is a block diagram of an ultrasound diagnostic apparatus 1000 according to an exemplary embodiment.

The ultrasound diagnostic apparatus 1000 may include an ultrasound transceiver 1100, an image processor 1200, and a display 1400.

The ultrasound transceiver 1100 may transmit an ultrasound signal to an object and receive an ultrasound echo signal reflected from the object.

The ultrasound transceiver 1100 may include a transmitter 1110 and a receiver 1120. Also, the ultrasound transceiver 1100 may include an ultrasound probe (not shown).

The transmitter 1110 may supply a drive signal to the probe so that the probe may transmit an ultrasound signal to the object. The receiver 1120 may receive from the probe an ultrasound echo signal reflected from the object and generate ultrasound data. In this case, the ultrasound transceiver 1100 may transmit an ultrasound signal to the object and received an ultrasound echo signal from the object, based on a beamforming parameter set in the ultrasound diagnostic apparatus 1000.

The image processor 1200 may generate an ultrasound image through a scan conversion process performed on the ultrasound data generated by the ultrasound transceiver 1100. The image processor 1200 may include a data processor 1210, and the data processor 1210 may include a frame generator 1213 and an image generator 1217.

The frame generator 1213 may generate a plurality of scanning lines forming a frame, based on a received ultrasound echo signal. For example, the frame generator 1213 may generate one scanning line or a plurality of scanning lines from one-time transmitted and/or received ultrasound data. When a plurality of scanning lines are generated from one-time transmitted and/or received ultrasound data, scanning lines properties of the scanning lines may be different.

When a frame is formed by generating one scanning line from one-time transmitted and/or received ultrasound data, scanning line properties of scanning lines may be similar to each other. However, when a new scanning line is generated by interpolating previously generated scanning lines or a plurality of scanning lines are generated from one-time transmitted and/or received ultrasound data at positions different from the position of an ultrasound transmitting beam, scanning line properties of scanning lines may be different. Also, when a new scanning line is generated by interpolating previously generated scanning lines, scanning line properties may differ according to an interpolation parameter. The difference in the scanning line properties according to the position of a scanning line in a frame may be represented by irregularity in a beam pattern of a scanning line.

When a frame in which a beam pattern of a scanning line is irregular is image-processed, a strict artifact may be generated. Among filters for algorithm image processing, an adaptive filter, for example, a Wiener filter, a Kalman filter, a Blind Deconvolution, a least mean squares (LMS) algorithm, and a recursive least squares (RLS) algorithm, which performs filtering on an ultrasound image by extracting a filter parameter from an image, may have a high probability of generating a strict artifact. In particular, for an image operation or image filter that has an influence in a direction perpendicular to a scanning line direction, a probability of generating a strict artifact may be high.

The frame generator 1213 may generate scanning lines having similar scanning line properties among a plurality of scanning lines, as one sub-frame, in order to make a beam pattern of a scanning line uniform. For example, the frame generator 1213 may generate at least one sub-frame by classifying, i.e., combining or sorting, a plurality of scanning lines into at least one group of scanning lines having similar scanning line properties.

In this case, the frame generator 1213 may determine beam patterns of scanning lines based on a beamforming method set in the ultrasound diagnostic apparatus 1000. For example, when the beamforming method is a radio-frequency (RF) interpolation method, the frame generator 1213 may analyze scanning line properties of a previously generated scanning line and a scanning line generated through interpolation to be different from each other. Also, in exemplary embodiments, the frame generator 1213 may analyze that scanning line properties of scanning lines generated through interpolation are different from each other.

The image generator 1217 may perform image processing on at least one generated sub-frame, and generate an ultrasound image corresponding to a frame by recombining scanning lines in an image processed sub-frame. In this case, since beam patterns of the scanning lines in a sub-frame are uniform, that is, scanning line properties of scanning lines in a sub-frame is similar to each other, even when image processing is performed on the sub-frame, if a strict artifact is not generated, an ultrasound image having no strict artifact may be generated by recombining the scanning lines in the sub-frame into one ultrasound image.

The display 1400 may display a generated ultrasound image.

Accordingly, the ultrasound diagnostic apparatus 1000 may generate an ultrasound image having no strict artifact by reflecting to image processing a phenomenon that a beam pattern of a scanning line becomes irregular by an RF interpolation method or a multi-beamforming method. Also, the ultrasound diagnostic apparatus 1000 may enhance performance of image processing. For example, the ultrasound diagnostic apparatus 1000 may improve estimation accuracy of a filter kernel.

In exemplary embodiments, no strict artifact is generated when a filter for image processing a two-dimensional (2D) filter or a three-dimensional (3D) filter.

Figure 2:
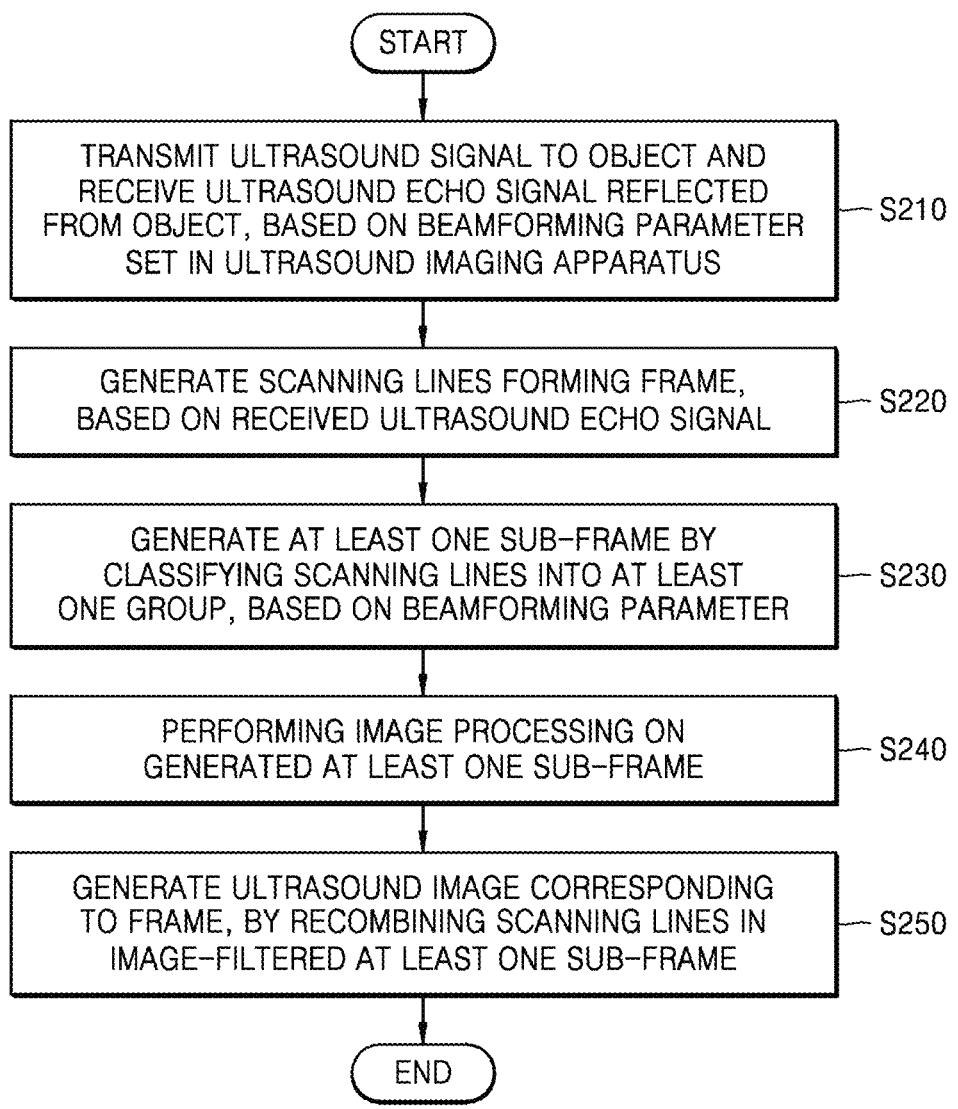
FIG. 2 is a flowchart of a method used by an ultrasound diagnostic apparatus to generate an ultrasound image having no strict artifact, according to an exemplary embodiment.

FIG. 2 is a flowchart of a method used by the ultrasound diagnostic apparatus 1000 to generate an ultrasound image having no strict artifact, according to an exemplary embodiment.

In an operation S210, the ultrasound diagnostic apparatus 1000 may transmit an ultrasound signal to an object and receive an ultrasound echo signal reflected from the object, based on a beamforming parameter set in the ultrasound diagnostic apparatus 1000.

A beamforming parameter may include at least one of a beamforming method, a beam steering direction, a depth of a focal point, a frequency of an ultrasound signal, and a size of an aperture, but not limited thereto. Also, a beamforming method may include an analog beamforming method, a digital beamforming method, a page rotation beamforming method, a multi-beamforming method, and an RF interpolation method.

In an operation S220, the ultrasound diagnostic apparatus 1000 may generate a plurality of scanning lines forming a frame, based on a received ultrasound echo signal.

The ultrasound diagnostic apparatus 1000 may generate a plurality of scanning lines from one-time transmitted and/or received ultrasound data.

For example, the ultrasound diagnostic apparatus 1000 may generate a plurality of scanning lines forming one frame, based on an RF interpolation method. For example, the ultrasound diagnostic apparatus 1000 may generate a first scanning line based on a first ultrasound echo signal corresponding to a first ultrasound signal, a second scanning line based on a second ultrasound echo signal corresponding to a second ultrasound signal, and at least one additional third scanning line by interpolating the first scanning line and the second scanning line, thereby generating a plurality of scanning lines.

Also, for example, the ultrasound diagnostic apparatus 1000 may generate a plurality of scanning lines forming one frame, via a multi-beamforming method. For example, the ultrasound diagnostic apparatus 1000 may transmit an ultrasound signal to an object and generate a plurality of scanning lines based on an ultrasound echo signal reflected according to one-time transmission of an ultrasound signal.

The RF interpolation method and the multi-beamforming method are beamforming methods that generate scanning lines more than the number of transmitted and/or received ultrasound signals, and may cause an effect of increasing density of scanning lines in an ultrasound image.

Also, adjacent scanning lines of the scanning lines generated by the RF interpolation method and the multi-beamforming method may have different scanning line properties. Also, scanning line properties of the scanning lines generated by the RF interpolation method and the multi-beamforming method may be represented by patterns. For example, in one frame, scanning line properties of odd-numbered scanning lines are the same, scanning line properties of even-numbered scanning lines are the same, and scanning line properties of the odd-numbered scanning lines and the even-numbered scanning lines may be different from each other. Also, for example, in one frame, scanning line properties may be similar in each of the $1^{st}$, $5^{th}$, $9^{th}$, $13^{th}$ . . . scanning lines, the $2^{nd}$, $6^{th}$, $10^{th}$, $14^{th}$ . . . scanning lines, the $3^{rd}$, $7^{th}$, $11^{th}$, $15^{th}$ . . . scanning lines, and the $4^{th}$, $8^{th}$, $12^{th}$, $16^{th}$ . . . scanning lines.

In an operation S230, the ultrasound diagnostic apparatus 1000 may generate at least one sub-frame by classifying a plurality of scanning lines into at least one group based on a beamforming parameter.

For example, the ultrasound diagnostic apparatus 1000 may obtain a type of a beamforming method by which a plurality of scanning lines are generated, based on a beamforming parameter, and classifying the scanning lines into at least one group to generate scanning lines having similar scanning line properties in one group, based on an obtained type of a beamforming method, thereby generating at least one sub-frame.

For example, when the beamforming method is an RF interpolation method, the ultrasound diagnostic apparatus 1000 may determine that scanning line properties of a previously generated scanning line and a scanning line generated through interpolation are different from each other. Accordingly, the ultrasound diagnostic apparatus 1000 may generate a first sub-frame formed with previously generated scanning lines and a second sub-frame formed with scanning lines generated through interpolation.

Also, for example, when the beamforming method is a 4-beamforming method, the ultrasound diagnostic apparatus 1000 may determine that, in one frame, scanning line properties are similar in each of the $1^{st}$, $5^{th}$, $9^{th}$, $13^{th}$ . . . scanning lines, the $2^{nd}$, $6^{th}$, $10^{th}$, $14^{th}$ . . . scanning lines, the $3^{rd}$, $7^{th}$, $11^{th}$, $15^{th}$ . . . scanning lines, and the $4^{th}$, $8^{th}$, $12^{th}$, $16^{th}$ . . . scanning lines, and may generate a first sub-frame formed with the (1+4n)th scanning lines, where n=0, 1, 2 . . . , a second sub-frame formed with the (2+4n)th scanning lines, a third sub-frame formed with the (3+4n)th scanning lines, and a fourth sub-frame formed with the (4+4n)th scanning lines.

In an operation S240, the ultrasound diagnostic apparatus 1000 may perform image processing on a generated sub-frame.

The image processing may include, for example, sharpening filtering, resolution adjustment filtering, and brightness adjustment filtering, but not limited thereto. The image processing may be performed with respect to scanning line data in a sub-frame.

The scanning line data may be in-phase quadrature (IQ) data, or complex number data, having image information, and may be pixel data, or real number data, in an ultrasound image.

In an operation S250, the ultrasound diagnostic apparatus 1000 may generate an ultrasound image corresponding to a frame, by recombining the scanning lines in an image-processed sub-framed.

The ultrasound diagnostic apparatus 1000 may generate an ultrasound image by rearranging scanning lines in the image processed sub-frame according to an order of the scanning lines before being classified into at least one group.

In an operation S260, the ultrasound diagnostic apparatus 1000 may display a generated ultrasound image.

The generated ultrasound image might not include a strict artifact. However, a strict artifact may be generated on an ultrasound image obtained by directly performing image processing with respect to the scanning lines on an original image.

Also, the ultrasound diagnostic apparatus 1000 may display an ultrasound image with an indicator indicating that a strict artifact of the ultrasound image is removed.

Also, the ultrasound diagnostic apparatus 1000 may first display an ultrasound image obtained by directly performing image processing with respect to the scanning lines on an original image, and display an ultrasound image where a strict artifact is removed, in response to a user's input selecting a button for removing a strict artifact.

Figure 3A:
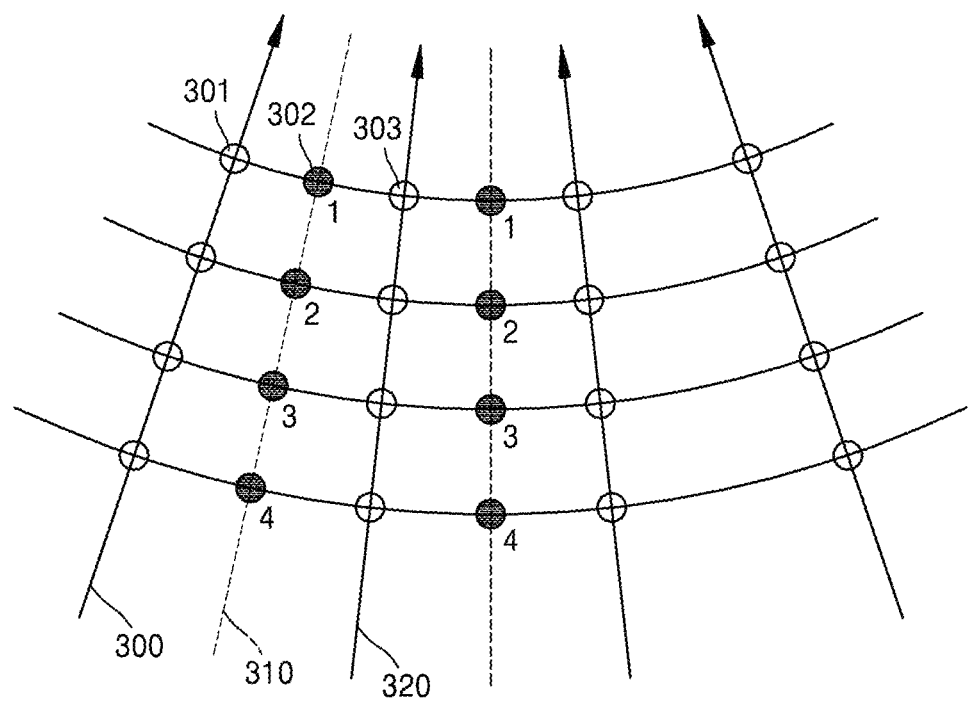
FIGS. 3A and 3B illustrate a method of generating an ultrasound image by generating more scanning lines than a transceiving number of an ultrasound signal, according to an exemplary embodiment.
Figure 3B:
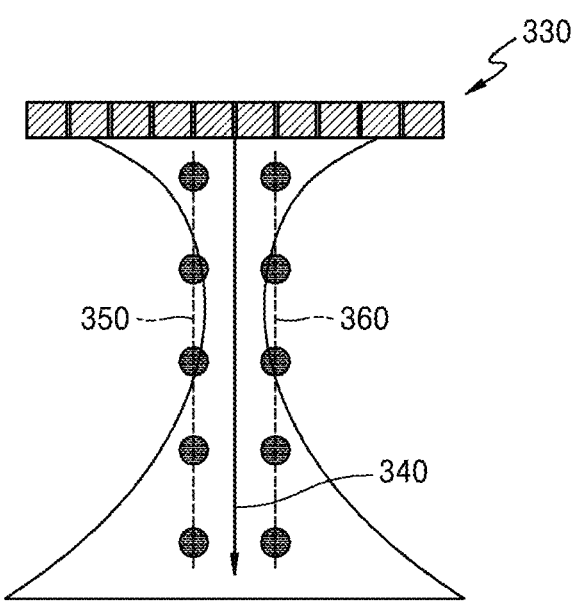

FIGS. 3A and 3B illustrate a method of generating an ultrasound image by generating scanning lines more than the number of transmitted and/or received ultrasound signals, according to an exemplary embodiment.

Referring to FIG. 3A, an RF interpolation method may include a method of generating a new scanning line by interpolating scanning lines. For example, the ultrasound diagnostic apparatus 1000 may generate at least one additional third scanning line 310 by interpolating a first scanning line 300 and a second scanning line 320. For example, the ultrasound diagnostic apparatus 1000 may generate the first position 302 of the at least one additional third scanning line 310 by interpolating the first position 301 of the first scanning line 300 and the first position 303 of the second scanning line 320. In this case, the first position 301 of the first scanning line 300, the first position 303 of the second scanning line 320, and the first position 302 of the at least one additional third scanning line 310 generated through interpolation are spaced apart by the same distance from an imaginary position Apex.

In this case, the first scanning line 300 and the second scanning line 320 may be scanning lines generated based on the ultrasound echo signal. The at least one additional third scanning line 310 may be a scanning line generated by interpolating previously generated scanning lines, and is not a scanning line generated directly from the ultrasound echo signal. Accordingly, the at least one additional third scanning line 310 that is generated through interpolation may have different scanning line properties from those of the first scanning line 300 and the second scanning line 320. In one frame, scanning line properties of the previously generated scanning lines, that is, the odd-numbered scanning lines in FIG. 3A, are the same, and scanning line properties of the scanning lines generated through interpolation, that is, the even-numbered scanning lines in FIG. 3B, are the same. Also, in some exemplary embodiments, the scanning line properties of the scanning lines generated through interpolation may be different from each other.

Referring to FIG. 3B, a multi-beamforming method may include a method of generating a plurality of scanning lines based on an ultrasound transmission beam 340.

For example, the ultrasound diagnostic apparatus 1000 may generate scanning lines by a 2-beamforming method. For example, the ultrasound diagnostic apparatus 1000 may transmit the ultrasound transmission beam 340 to an object by focusing an ultrasound signal generated by a transducer 330 and generate two scanning lines 350 and 360 based on an ultrasound echo signal reflected from the object. In this case, the ultrasound diagnostic apparatus 1000 may generate the first scanning line 350 at the right of the ultrasound transmission beam 340 and the second scanning line 360 at the left of the ultrasound transmission beam 340. In this case, the first scanning line 350 and the second scanning line 360 may have different scanning line properties and, in one frame, scanning line properties of the odd-numbered scanning lines may be the same and scanning line properties of the even-numbered scanning lines may be the same.

Also, for example, the ultrasound diagnostic apparatus 1000 may generate scanning lines by a 3-beamforming method. For example, the ultrasound diagnostic apparatus 1000 may transmit the ultrasound transmission beam 340 to the object by focusing an ultrasound signal generated by the transducer 330 and generate three scanning lines based on an ultrasound echo signal reflected from the object. For example, the ultrasound diagnostic apparatus 1000 may generate one scanning line at the right of the ultrasound transmission beam 340, one scanning line 360 at the left of the ultrasound transmission beam 340, and one scanning line at the position of the ultrasound transmission beam 340. In this case, scanning line properties of each of the three scanning lines may be different from one another and, in one frame, scanning line properties of the (1+3n)th scanning lines, where n=0, 1, 2 . . . , may be the same, scanning line properties of the (2+3n)th scanning lines may be the same, and scanning line properties of the (3+3n)th scanning lines may be the same.

Also, for example, the ultrasound diagnostic apparatus 1000 may generate scanning lines by a 4 multi-beamforming method. For example, the ultrasound diagnostic apparatus 1000 may transmit the ultrasound transmission beam 340 to the object by focusing an ultrasound signal generated by the transducer 330 and generate four scanning lines based on an ultrasound echo signal reflected from the object. In this case, the ultrasound diagnostic apparatus 1000 may generate two scanning lines at the right of the ultrasound transmission beam 340 and two scanning lines at the left of the ultrasound transmission beam 340. In this case, scanning line properties of each of the four scanning line may be different from one another and, in one frame, scanning line properties of the (1+4n)th scanning lines, where n=0, 1, 2 . . . , may be the same, scanning line properties of the (2+4n)th scanning lines may be the same, scanning line properties of the (3+4n)th scanning lines may be the same, and scanning line properties of the (4+4n)th scanning lines may be the same.

Figure 4A:
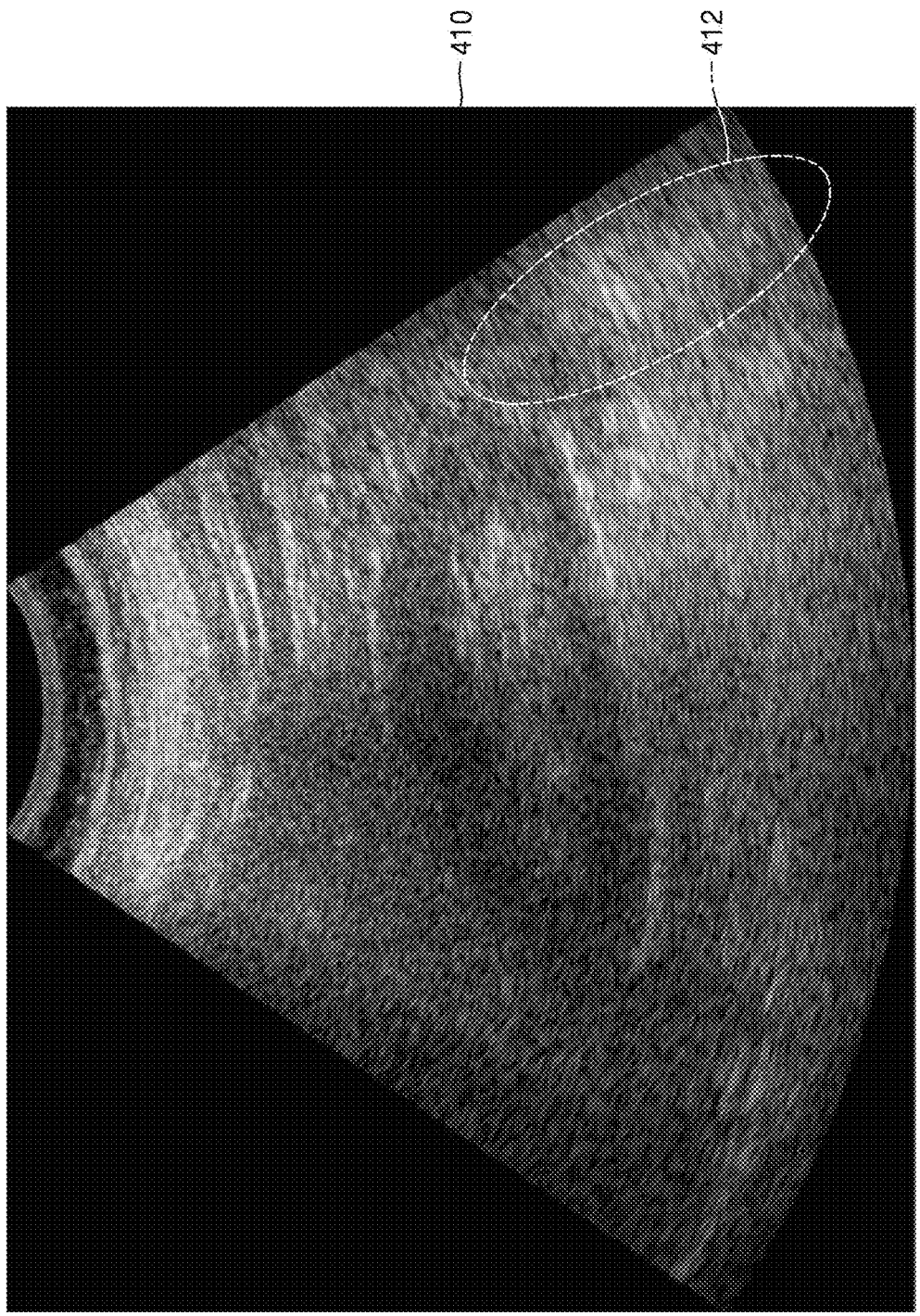
FIGS. 4A and 4B are images for describing generation of a strict artifact in an ultrasound image when adjacent scanning lines having different scanning line properties are image-processed, according to an exemplary embodiment.
Figure 4B:

FIGS. 4A and 4B are images for describing generation of a strict artifact in an ultrasound image when adjacent scanning lines having different scanning line properties are image-processed, according to an exemplary embodiment.

FIG. 4A is an original ultrasound image 410 before image processing. A beamforming method of the original ultrasound image 410 may be a multi-beamforming method or an RF interpolation method. When the beamforming method is a multi-beamforming method or an RF interpolation method, scanning line properties of adjacent scanning lines may be different from each other.

FIG. 4B is an ultrasound image 420 after image processing. The ultrasound diagnostic apparatus 1000 may perform image processing on the original ultrasound image 410. The image processing may include, for example, sharpening filtering, resolution adjustment filtering, and brightness adjustment filtering, but not limited thereto.

As the original ultrasound image 410 in which scanning line properties of adjacent scanning lines are different from each other is image-processed, a strict artifact 422 may be generated on the ultrasound image 420, on the whole. The strict artifact 422 may be a lengthy strip pattern generated in a scanning line direction.

When the original ultrasound image 410 before image processing of FIG. 4A and the ultrasound image 420 after image processing of FIG. 4B are compared with each other, the ultrasound image 420 after image processing is sharpener and has a higher resolution, compared to the original ultrasound image 410. However, it may be seen that the strict artifact 422, which has not been present in the original ultrasound image 410, is generated in the ultrasound image 420 after image processing. It may be seen that no strict artifact exists in an area 412 in the original ultrasound image 410, which corresponds to an area where the strict artifact 422 is generated.

Figure 5:
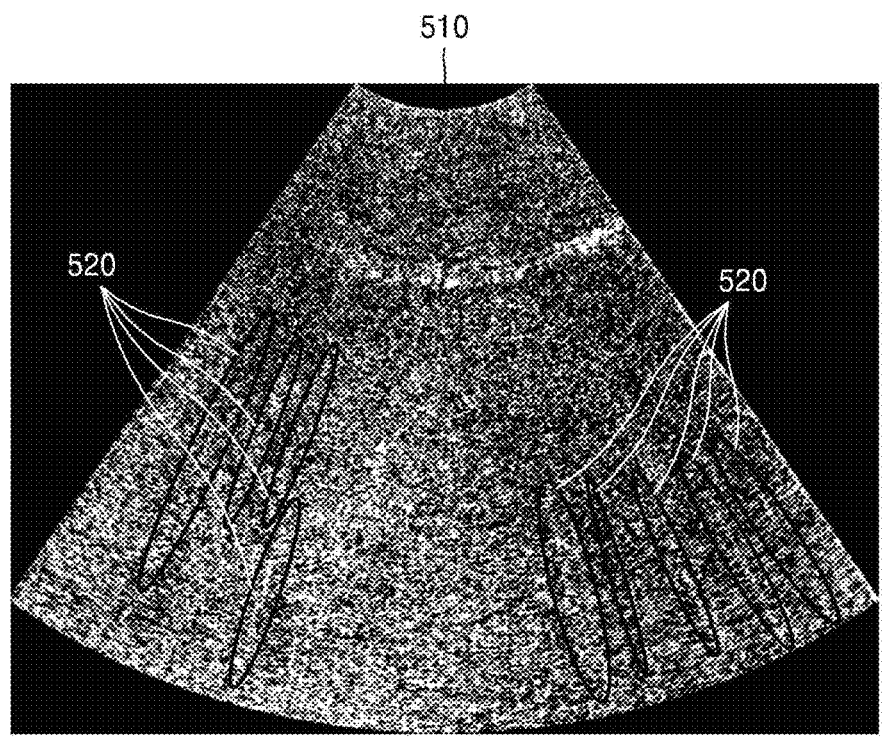
FIG. 5 is an image for describing generation of a strict artifact in an ultrasound image when adjacent scanning lines having different scanning line properties are image-processed, according to an exemplary embodiment.

FIG. 5 is an image for describing generation of a strict artifact in an ultrasound image when adjacent scanning lines having different scanning line properties are image-processed, according to an exemplary embodiment.

Referring to FIG. 5, a differential ultrasound image 510 may be an image showing a difference between the ultrasound image 420 after image processing and the original ultrasound image 410. The differential ultrasound image 510 may include a long and thin strip pattern 520 in a scanning line due to a strict artifact existing in the ultrasound image 420 after image processing.

Figure 6:
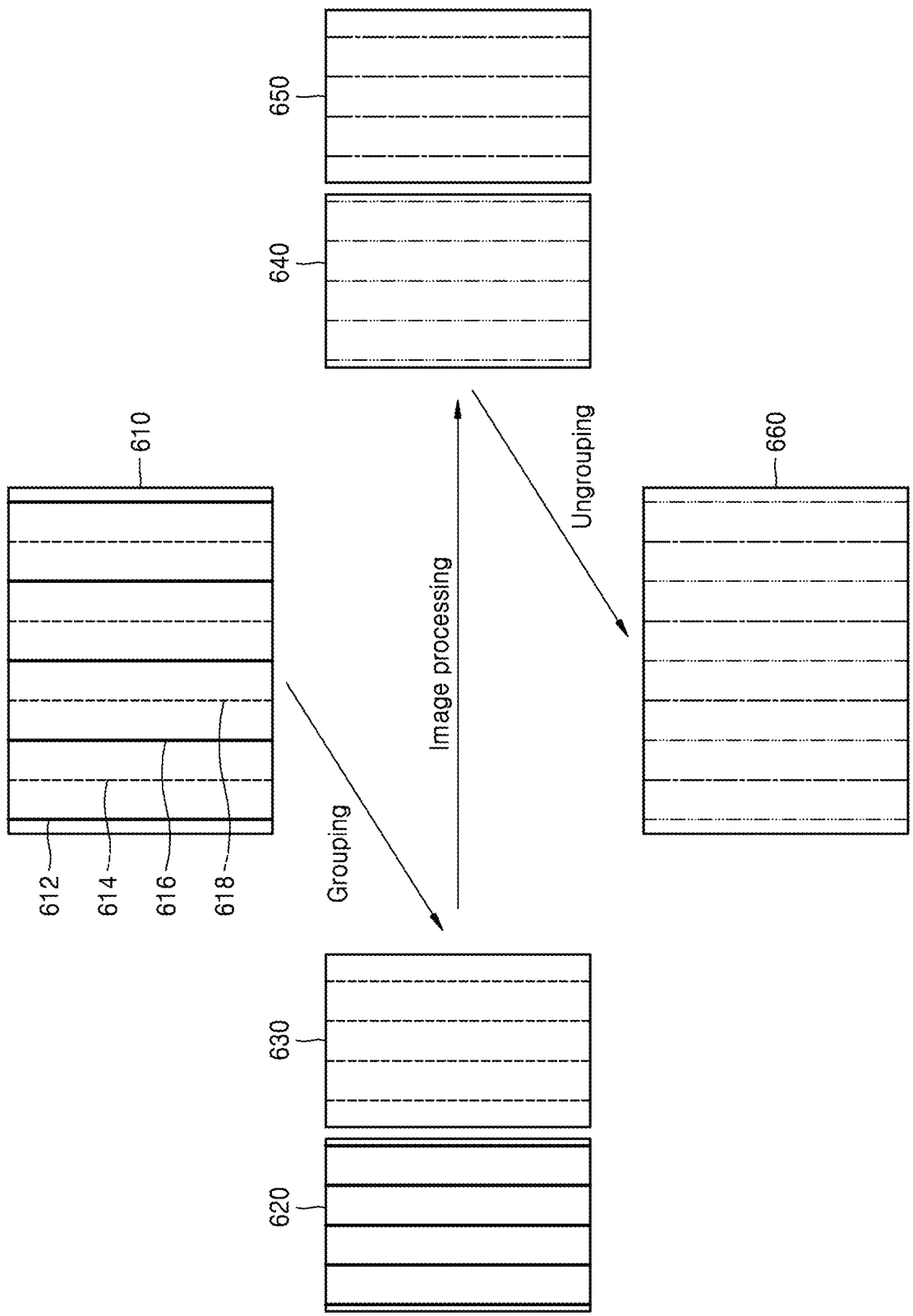
FIG. 6 illustrates a method of performing image processing to prevent generation of a strict artifact, the method being used by an ultrasound diagnostic apparatus that performs image processing on a scanning line based on scanning line properties, according to an exemplary embodiment.

FIG. 6 illustrates a method of performing image processing to prevent generation of a strict artifact as the ultrasound diagnostic apparatus 1000 performs image processing on a scanning line based on scanning line properties, according to an exemplary embodiment.

Referring to FIG. 6, the ultrasound diagnostic apparatus 1000 may generate an ultrasound image 660 having no strict artifact, by classifying a plurality of scanning lines in a frame 610 into at least one group based on a beamforming parameter to generate at least one sub-frame, that is, sub-frames 620 and 630 in the present exemplary embodiment, performing image-processing on a generated sub-frame, and recombining scanning lines in at least one image-processed sub-frame, that is, a first sub-frame 640 and a second sub-frame 650 in the present exemplary embodiment.

A beamforming parameter may include at least one of a beamforming method, a beam steering direction, a depth of a focal point, a frequency of an ultrasound signal, and a size of an aperture, but not limited thereto. Also, beamforming method may include an analog beamforming method, a digital beamforming method, a page rotation beamforming method, a multi-beamforming method, and an RF interpolation method.

The ultrasound diagnostic apparatus 1000 may generate a plurality of scanning lines forming the frame 610, based on a beamforming method. When the beamforming method is a multi-beamforming method or an RF interpolation method, scanning line properties of adjacent scanning lines of a plurality of scanning lines may be different from each other. For example, when the beamforming method is an RF interpolation method in which one scanning line is additionally generated through interpolation, a first scanning line 612 and a third scanning line 616 may be scanning lines generated by being directly decoded from an ultrasound echo signal, and a second scanning line 614 may be a scanning line generated by interpolating the first scanning line 612 and the third scanning line 616. Accordingly, scanning line properties of the first scanning line 612 and the third scanning line 616 are similar to each other, and scanning line properties of the second scanning line 614 and the fourth scanning line 618 may be similar to each other.

Also, when the beamforming method is a 2 multi-beamforming method, the first scanning line 612 and the second scanning line 614 may be two scanning lines generated based on an ultrasound echo signal received from the object after transmitting one ultrasound transmission beam having a focal point between the first scanning line 612 and the second scanning line 614 to the object. Accordingly, scanning line properties of the first scanning line 612 and the third scanning line 616 may be similar to each other and scanning line properties of the second scanning line 614 and the fourth scanning line 618 may be similar to each other.

Also, when the beamforming method is a 4 multi-beamforming method, four scanning lines may be generated corresponding to one ultrasound transmission beam. In this case, scanning line properties of a first scanning line and a fifth scanning line scanning line properties may be similar to each other, and scanning line properties of a second scanning line and a sixth scanning line may be similar to each other.

Accordingly, the ultrasound diagnostic apparatus 1000 may classify scanning lines having similar scanning line properties into one group, based on a beamforming parameter set in the ultrasound diagnostic apparatus 1000.

For example, when the beamforming method is an RF interpolation method that generates an additional scanning line by interpolating one scanning line or a 2 multi-beamforming method, the ultrasound diagnostic apparatus 1000 may classify the first scanning line 612 and the third scanning line 616, which are odd-numbered scanning lines, into a first group, and the second scanning line 614 and the fourth scanning line 618, which are even-numbered scanning lines, into a second group, based on an order of scanning lines.

As a plurality of scanning lines in a frame are classified into the first group and the second group, the ultrasound diagnostic apparatus 1000 may generates a first sub-frame 620 based on a scanning line of the first group and a second sub-frame 630 based on a scanning line of the second group second group 630.

After generating the first sub-frame 620 and the second sub-frame 630 by classifying a plurality of scanning lines in the frame 610, the ultrasound diagnostic apparatus 1000 may perform image processing on each of the first sub-frame 620 and the second sub-frame 630 without performing image processing on the frame 610. The image processing may include all filtering techniques applied to an image to improve quality of the image, for example, sharpening filtering, resolution adjustment filtering, and brightness adjustment filtering, but not limited thereto.

The ultrasound diagnostic apparatus 1000 may generate the ultrasound image 660 corresponding to the frame 610 by recombining scanning lines in the first sub-frame 640 and the second sub-frame 650 that are image-processed.

For example, the ultrasound diagnostic apparatus 1000 may generate the ultrasound image 660 corresponding to the frame 610 by recombining the scanning lines in at least one of the first and second sub-frames 640 and 650 that are image-processed, according to the order of the scanning lines in the frame 610 before being classified into at least one group.

Figure 7:
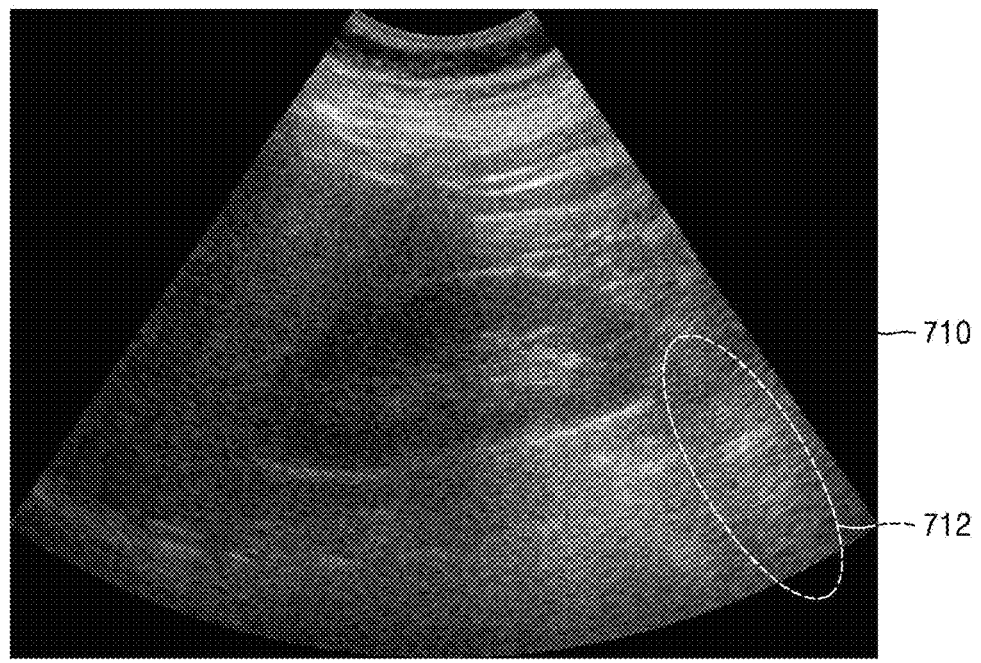
FIG. 7 is an ultrasound image including no strict artifact after image processing is performed thereon, according to an exemplary embodiment.

FIG. 7 is an ultrasound image on which no strict artifact is generated after image processing is performed, according to an exemplary embodiment.

Referring to FIG. 7, the ultrasound diagnostic apparatus 1000 may generate at least one sub-frame by classifying the scanning lines in the original ultrasound image 410 of FIG. 4A based on the beamforming method set in the ultrasound diagnostic apparatus 1000, and generate an ultrasound image 710 where no strict artifact is generated, by performing image processing on a generated sub-frame.

While the ultrasound image 710 of FIG. 7 becomes sharper and has a higher resolution, like the ultrasound image 420 of FIG. 4B after the image-processing, it may be seen that no strict artifact is generated in an area 712 in the ultrasound image 710 of FIG. 7 corresponding to the ultrasound image 420 of FIG. 4B after the image-processing.

Figure 8A:
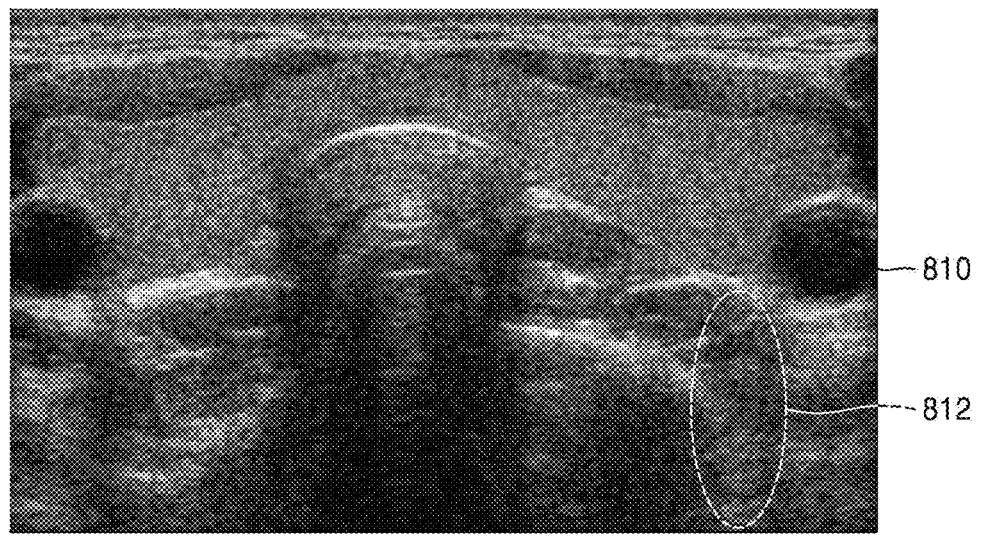
FIGS. 8A, 8B, and 8C are ultrasound images for comparing an ultrasound image including a strict artifact and an ultrasound image including no strict artifact, according to an exemplary embodiment.
Figure 8B:
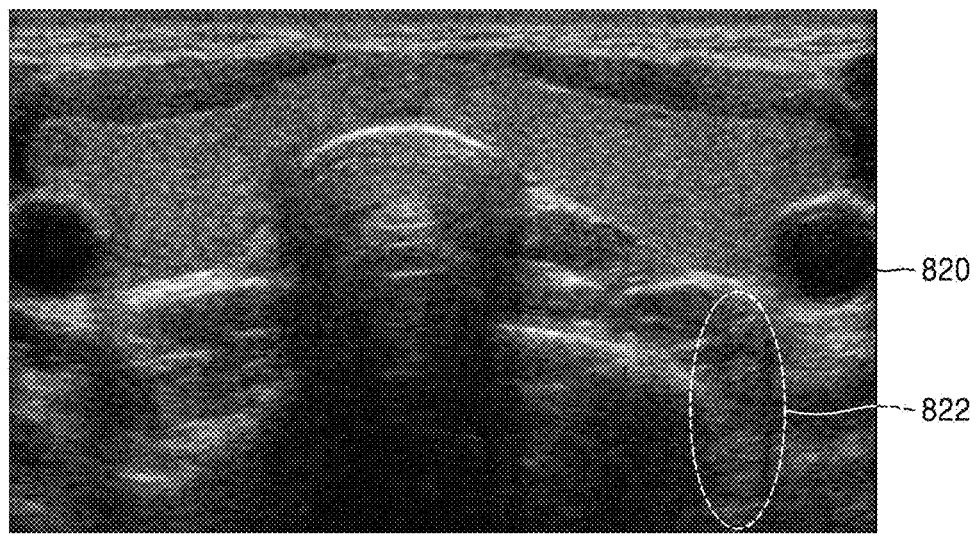
Figure 8C:
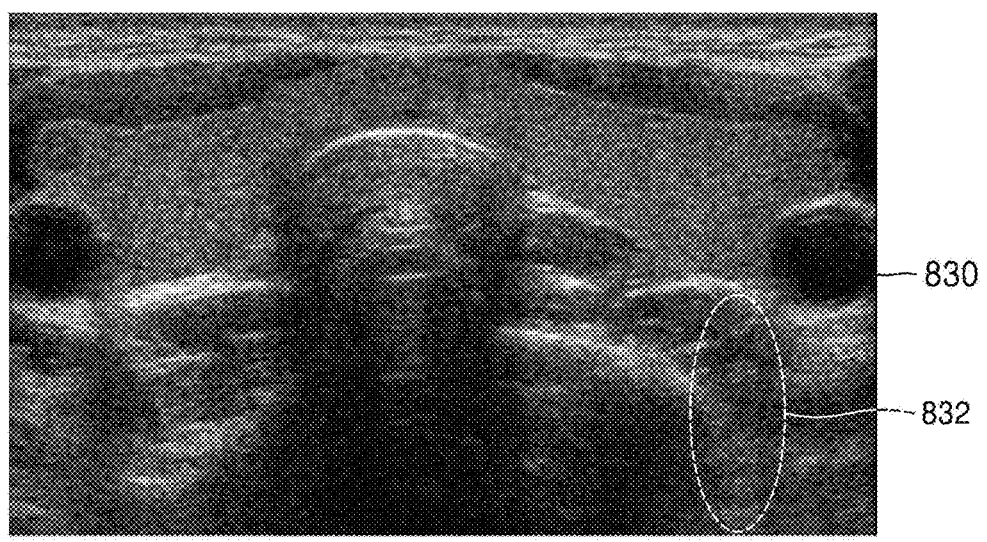

FIGS. 8A, 8B, and 8C are ultrasound images for comparing an ultrasound image where a strict artifact is generated and an ultrasound image where a strict artifact is not generated, according to an exemplary embodiment.

Referring to FIGS. 8A, 8B, and 8C, the ultrasound diagnostic apparatus 1000 may generate a plurality of scanning lines based on a multi-beamforming method or an RF interpolation method, and generate an original ultrasound image 810 based on generated scanning lines.

The ultrasound diagnostic apparatus 1000 may perform image-processing on the original ultrasound image 810. In the scanning lines generated by a multi-beamforming method or an RF interpolation method, scanning line properties between adjacent scanning lines may be different from each other. Accordingly, a strict artifact may be generated in an ultrasound image 820 after image-processing is performed. For example, while no strict artifact exists in a lower right area 812 of the original ultrasound image 810, it may be seen that a strict artifact is generated in a lower right area 822 of the ultrasound image 820 after image-processing is performed.

When the beamforming method is set to be a multi-beamforming method or an RF interpolation method, the ultrasound diagnostic apparatus 1000 may generate an ultrasound image 830 where no strict artifact exists, by classifying the scanning lines in the original ultrasound image 810 into at least one sub-frame and performing image-processing on the sub-frame, based on a set beamforming method.

It may be seen that no strict artifact exists in a lower right area 832 of an image 830 in which image-processing is performed on the sub-frame.

Figure 9:
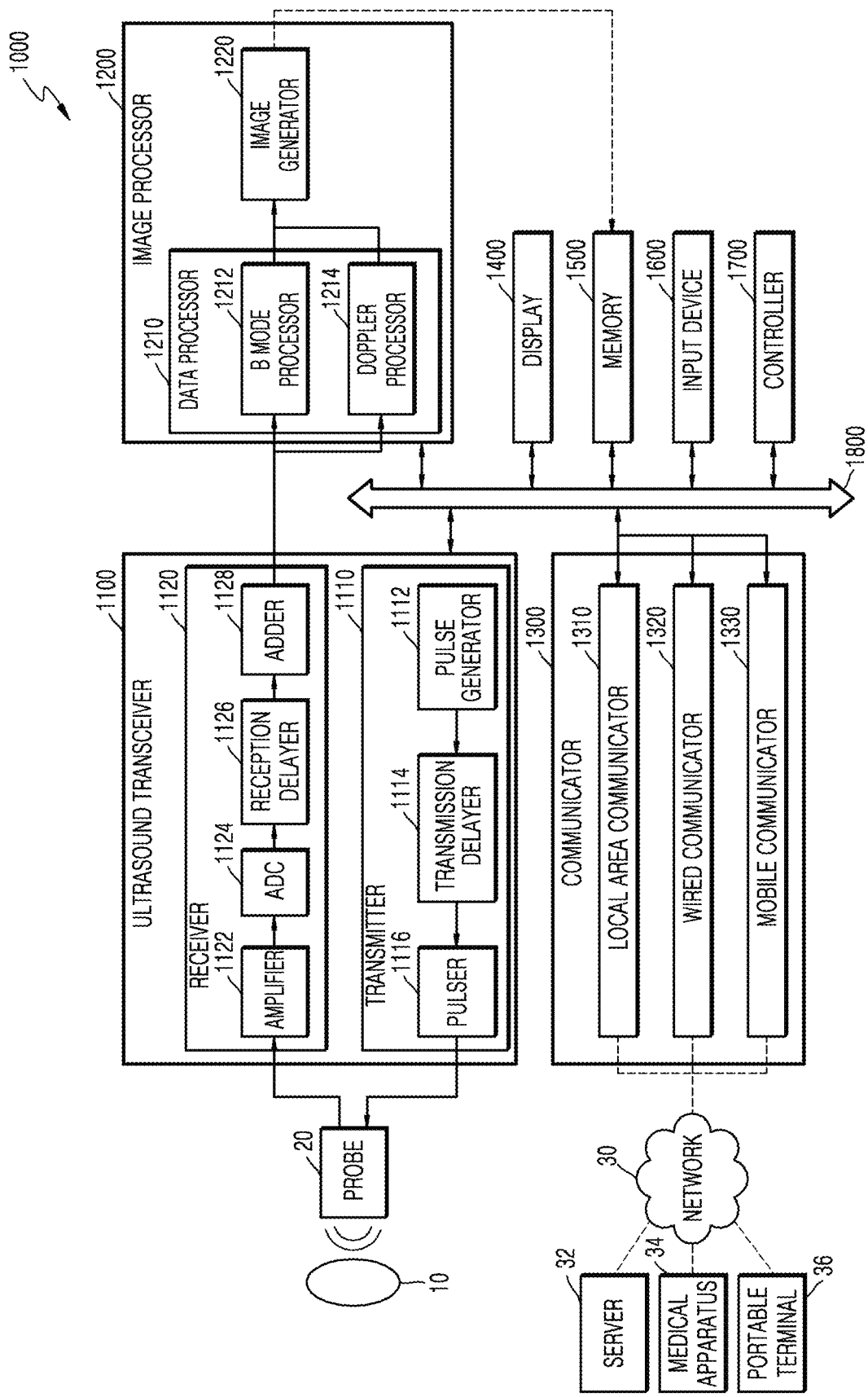
FIG. 9 is a block diagram of an ultrasound diagnostic apparatus according to an exemplary embodiment.

FIG. 9 is a block diagram showing a configuration of an ultrasound diagnostic apparatus 1000 according to an exemplary embodiment. Referring to FIG. 1, the ultrasound diagnostic apparatus 1000 may include a probe 20, an ultrasound transceiver 1100, an image processor 1200, a communicator 1300, a display 1400, a memory 1500, an input device 1600, and a controller 1700, which may be connected to one another via buses 1800.

The ultrasound diagnostic apparatus 1000 may be a cart type apparatus or a portable type apparatus. Examples of portable ultrasound diagnostic apparatuses 1000 may include, but are not limited to, a picture archiving and communication system (PACS) viewer, a smartphone, a laptop computer, a personal digital assistant (PDA), and a tablet PC.

The probe 20 transmits ultrasound waves to an object 10 in response to a driving signal applied by the ultrasound transceiver 1100 and receives echo signals reflected by the object 10. The probe 20 includes a plurality of transducers, and the plurality of transducers oscillate in response to electric signals and generate acoustic energy, that is, ultrasound waves. The probe 20 may be connected to the main body of the ultrasound diagnostic apparatus 1000 by wire or wirelessly, and according to exemplary embodiments, the ultrasound diagnostic apparatus 1000 may include a plurality of probes 20.

A transmitter 1110 supplies a driving signal to the probe 20. The transmitter 1110 includes a pulse generator 1112, a transmission delayer 1114, and a pulser 1116. The pulse generator 1112 generates pulses for forming transmission ultrasound waves based on a predetermined pulse repetition frequency (PRF), and the transmission delayer 1114 delays the pulses by delay times necessary for determining transmission directionality. The pulses which have been delayed correspond to a plurality of piezoelectric vibrators included in the probe 20, respectively. The pulser 1116 applies a driving signal (or a driving pulse) to the probe 20 based on timing corresponding to each of the pulses which have been delayed.

A receiver 1120 generates ultrasound data by processing echo signals received from the probe 20. The receiver 120 may include an amplifier 1122, an analog-to-digital converter (ADC) 1124, a reception delayer 1126, and an adder 1128. The amplifier 1122 amplifies echo signals in each channel, and the ADC 1124 performs analog-to-digital conversion with respect to the amplified echo signals. The reception delayer 1126 delays digital echo signals output by the ADC 1124 by delay times necessary for determining reception directionality, and the adder 1128 generates ultrasound data by summing the echo signals processed by the reception delayer 1126. In some embodiments, the receiver 1120 may not include the amplifier 1122. In other words, if the sensitivity of the probe 20 or the capability of the ADC 1124 to process bits is enhanced, the amplifier 1122 may be omitted.

The image processor 1200 generates an ultrasound image by scan-converting ultrasound data generated by the ultrasound transceiver 1100. The ultrasound image may be a grayscale ultrasound image obtained by scanning an object in an amplitude (A) mode, a brightness (B) mode, and a motion (M) mode, and a Doppler image showing a movement of an object via a Doppler effect. The Doppler image may be a blood flow Doppler image showing flow of blood (also referred to as a color Doppler image), a tissue Doppler image showing a movement of tissue, or a spectral Doppler image showing a moving speed of an object as a waveform.

A B mode processor 1212 extracts B mode components from ultrasound data and processes the B mode components. An image generator 1220 may generate an ultrasound image indicating signal intensities as brightness based on the extracted B mode components 1212.

Similarly, a Doppler processor 1214 may extract Doppler components from ultrasound data, and the image generator 1220 may generate a Doppler image indicating a movement of an object as colors or waveforms based on the extracted Doppler components.

According to an exemplary embodiment, the image generator 1220 may generate a 3D ultrasound image via volume-rendering with respect to volume data and may also generate an elasticity image by imaging deformation of the object 10 due to pressure. The image generator 1220 may display various pieces of additional information in an ultrasound image by using text and graphics. In addition, the generated ultrasound image may be stored in the memory 1500.

A display 1400 displays the generated ultrasound image and/or various pieces of information processed by the ultrasound diagnostic apparatus 1000 on a screen image via a graphical user interface (GUI). The ultrasound diagnostic apparatus 1000 may include two or more displays 1400 according to exemplary embodiments.

The communicator 1300 is connected to a network 30 by wire or wirelessly to communicate with an external device or a server. The communicator 1300 may exchange data with a hospital server or another medical apparatus in a hospital, which is connected thereto via a PACS. The communicator 1300 may perform data communication according to the digital imaging and communications in medicine (DICOM) standard.

The communicator 1300 may transmit or receive data related to diagnosis of an object, e.g., an ultrasound image, ultrasound data, and Doppler data of the object, via the network 30 and may also transmit or receive medical images captured by another medical apparatus, e.g., a computed tomography (CT) apparatus, a magnetic resonance imaging (MRI) apparatus, or an X-ray apparatus. The communicator 1300 may receive information about a diagnosis history or medical treatment schedule of a patient from a server and utilizes the received information to diagnose the patient. The communicator 1300 may perform data communication with a server or a medical apparatus in a hospital and also with a portable terminal of a medical doctor or patient.

The communicator 1300 is connected to the network 30 by wire or wirelessly to exchange data with a server 32, a medical apparatus 34, or a portable terminal 36. The communicator 1300 may include one or more components for communication with external devices. For example, the communicator 1300 may include a local area communicator 1310, a wired communicator 1320, and a mobile communicator 1330.

The local area communicator 1310 refers to a module for local area communication within a predetermined distance. Examples of local area communication techniques according to an exemplary embodiment may include, but are not limited to, wireless LAN, Wi-Fi, Bluetooth, ZigBee, Wi-Fi Direct (WFD), ultra-wideband (UWB), infrared data association (IrDA), Bluetooth low energy (BLE), and near field communication (NFC).

The wired communicator 1320 refers to a module for communication using electric signals or optical signals. Examples of wired communication techniques according to an exemplary embodiment may include communication via a twisted pair cable, a coaxial cable, an optical fiber cable, and an Ethernet cable.

The mobile communicator 1330 transmits or receives wireless signals to or from at least one selected from a base station, an external terminal, and a server on a mobile communication network. The wireless signals may be voice call signals, video call signals, or various types of data for transmission and reception of text/multimedia messages.

The memory 1500 stores various data processed by the ultrasound diagnostic apparatus 1000. For example, the memory 1500 may store medical data related to diagnosis of an object, such as ultrasound data and an ultrasound image that are input or output, and may also store algorithms or programs which are to be executed in the ultrasound diagnostic apparatus 1000.

The memory 1500 may be any of various storage media, e.g., a flash memory, a hard disk drive, EEPROM, etc. The ultrasound diagnostic apparatus 1000 may utilize web storage or a cloud server that performs the storage function of the memory 400 online.

The input device 1600 refers to a means via which a user inputs data for controlling the ultrasound diagnostic apparatus 1000. The input device 1600 may include hardware components, such as a keypad, a mouse, a touch pad, a touch screen, and a jog switch. However, exemplary embodiments are not limited thereto, and the input device 1600 may further include any of various other input units including an electrocardiogram (ECG) measuring module, a respiration measuring module, a voice recognition sensor, a gesture recognition sensor, a fingerprint recognition sensor, an iris recognition sensor, a depth sensor, a distance sensor, etc.

The controller 1700 may control all operations of the ultrasound diagnostic apparatus 1000. In other words, the controller 1700 may control operations among the probe 20, the ultrasound transceiver 1100, the image processor 1200, the communicator 1300, the display 1400, the memory 1500, and the input device 1600 shown in FIG. 9.

All or some of the probe 20, the ultrasound transceiver 1100, the image processor 1200, the communicator 1300, the display 1400, the memory 1500, the input device 1600, and the controller 1700 may be implemented as software modules. Also, at least one of the ultrasound transceiver 1100, the image processor 1200, and the communicator 1300 may be included in the controller 1700; however, an exemplary embodiment is not limited thereto.

The foregoing exemplary embodiments and advantages are merely exemplary and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. An ultrasound imaging apparatus comprising:
an ultrasound transceiver configured to transmit an ultrasound signal to an object and receive an ultrasound echo signal reflected from the object, based on a beamforming parameter of the ultrasound imaging apparatus; and
an image processor configured to generate scanning lines forming a frame based on the received ultrasound echo signal and the beamforming parameter including a type of beamforming method, wherein the type of beamforming method indicates an analog beamforming method, a digital beamforming method, page rotation beamforming method or multi-beamforming method,
determine a beam pattern for the generated scanning lines, based on the beamforming parameter, wherein the beam pattern indicates a method for generating the scanning lines,
generate sub-frames by sorting the scanning lines into respective groups having the scanning lines with a same beam pattern,
perform image-processing of the generated sub-frames,
recombine the scanning lines from the image-processed sub-frames, and
generate an ultrasound medical image corresponding to the frame based on the recombined scanning lines.

2. The ultrasound imaging apparatus of claim 1, further comprising a display configured to display the generated ultrasound medical image.

3. The ultrasound imaging apparatus of claim 1, wherein the ultrasound signal comprises a first ultrasound signal and a second ultrasound signal having focal points at different positions, and
the image processor is configured to generate the scanning lines by generating a first scanning line based on a first ultrasound echo signal corresponding to the first ultrasound signal, generating a second scanning line based on a second ultrasound echo signal corresponding to the second ultrasound signal, and generating a third scanning line extending in-between and having a different beam pattern than that of the first scanning line and the second scanning line, by interpolating the first scanning line and the second scanning line, generate a first sub-frame, among the sub-frames, by combining the first scanning line and the second scanning line, generate a second sub-frame, among the sub-frames, by including the third scanning line, perform the image-processing on the first sub-frame and the second sub-frame, rearrange the first scanning line, the second scanning line, and the third scanning line from the image-processed first and second sub-frames in an order of the first scanning line, the third scanning line, and the second scanning line, and generate the ultrasound medical image corresponding to the frame, based on the rearranged first scanning line, third scanning line, and second scanning line.

4. The ultrasound imaging apparatus of claim 1, wherein the image processor is configured to generate the scanning lines corresponding to a one-time transmitted ultrasound signal, based on one or more of the received ultrasound echo signals.

5. The ultrasound imaging apparatus of claim 1, wherein the image processor is configured to generate the ultrasound medical image by rearranging the scanning lines in the image-processed sub-frames in an order in which the scanning lines were originally arranged, prior to have been sorted into the respective groups.

6. An ultrasound imaging method comprising:
transmitting an ultrasound signal to an object and receiving an ultrasound echo signal reflected from the object, based on a beamforming parameter of an ultrasound imaging apparatus;
generating scanning lines forming a frame based on the received ultrasound echo signal and the beamforming parameter including a type of beamforming method, wherein the type of beamforming method indicates an analog beamforming method, a digital beamforming method, page rotation beamforming method or multi-beamforming method;

determining a beam pattern for the generated scanning lines, based on the beamforming parameter, wherein the beam pattern indicates a method for generating the scanning lines;

generating sub-frames by sorting the scanning lines into respective groups having the scanning lines with a same beam pattern;

performing image-processing of the generated sub-frames;

recombining the scanning lines from the image-processed sub-frames; and generating an ultrasound medical image corresponding to the frame based on the recombined scanning lines.

7. The ultrasound imaging method of claim 6, further comprising displaying the generated ultrasound medical image.

8. The ultrasound imaging method of claim 6, wherein the ultrasound signal comprises a first ultrasound signal and a second ultrasound signal having focal points at different positions, and the ultrasound imaging method further comprises:

generating a first scanning line based on a first ultrasound echo signal corresponding to the first ultrasound signal;

generating a second scanning line based on a second ultrasound echo signal corresponding to the second ultrasound signal;

generating a third scanning line extending in-between and having a different beam pattern than that of the first scanning line and the second scanning line, by interpolating the first scanning line and the second scanning line;

generating a first sub-frame, among the sub-frames, by combining the first scanning line and the second scanning line, and generating a second sub-frame, among the sub-frames, by including the third scanning line;

performing the image-processing on the first sub-frame and the second sub-frame;

rearranging the first scanning line, the second scanning line, and the third scanning line from the image-processed first and second sub-frames in an order of the first scanning line, the third scanning line, and the second scanning line; and generating the ultrasound medical image corresponding to the frame, based on the rearranged first scanning line, third scanning line, and second scanning line.

9. The ultrasound imaging method of claim 6, wherein the generating the scanning lines comprises generating the scanning lines corresponding to a one time transmitted ultrasound signal, based on one or more of the received ultrasound echo signals.

10. The ultrasound imaging method of claim 6, wherein the recombining the scanning lines comprises:

rearranging the scanning lines in the image-processed sub-frames in an order in which the scanning lines were originally arranged, prior to have been sorted into the respective groups.

* * * * *